United States Patent [19]

Huhn

[11] Patent Number: 5,119,825
[45] Date of Patent: Jun. 9, 1992

[54] MULTI-FUNCTIONAL PATIENT VALVE

[75] Inventor: James M. Huhn, North Oaks, Minn.

[73] Assignee: Medical Graphics Corporation, St. Paul, Minn.

[21] Appl. No.: 660,673

[22] Filed: Feb. 25, 1991

[51] Int. Cl.⁵ .......................................... A61M 16/20
[52] U.S. Cl. .................................. 128/716; 128/725; 128/914; 128/205.17; 137/861; 137/885
[58] Field of Search .................. 128/716, 718–720, 128/724–730, 909, 200.11–200.13, DIG. 12, DIG. 13; 251/4–7; 73/23.3; 137/637, 637.05, 861; 604/865, 250

[56] References Cited

U.S. PATENT DOCUMENTS

| | | | |
|---|---|---|---|
| 2,371,434 | 3/1945 | Eppler | 51/12 |
| 2,624,364 | 1/1953 | Detlefsen | 137/609 |
| 3,075,551 | 1/1963 | Smith, et al. | 137/609 |
| 3,306,283 | 2/1967 | Arp | 128/719 |
| 3,511,469 | 5/1970 | Bell | 251/7 |
| 3,724,807 | 4/1973 | Jackson | 251/7 |
| 3,916,948 | 11/1975 | Benjamin | 137/861 |
| 3,974,858 | 8/1976 | Nielsen | 137/606 |
| 4,172,580 | 10/1979 | Raftis et al. | 251/7 |
| 4,607,659 | 2/1986 | Cole | 137/454.2 |
| 4,635,897 | 1/1987 | Gallant | 251/5 |
| 4,807,845 | 2/1989 | Darnall | 251/7 |
| 4,899,783 | 2/1990 | Yusko, Jr. et al. | 251/7 |
| 4,903,693 | 2/1990 | Yasue | 128/716 |
| 4,921,206 | 5/1990 | Dunstan et al. | 251/7 |
| 5,046,491 | 9/1991 | Derrick | 128/716 |

Primary Examiner—William E. Kamm
Assistant Examiner—Jeffrey R. Jastrzab
Attorney, Agent, or Firm—Haugen and Nikolai

[57] ABSTRACT

A single-use, disposable patient valve for use in cardiopulmonary test apparatus comprises a molded, flexible, elastomeric tubular body of a cruciform shape an cooperating with the stem portion of the cross are first and second selective actuatable clamps which, when actuated, pinch off the flow of gases across the pinched portion.

13 Claims, 1 Drawing Sheet

MULTI-FUNCTIONAL PATIENT VALVE

BACKGROUND OF THE INVENTION

1. Field of the Invention

This invention relates generally to cardiopulmonary test apparatus, and more particularly to a low-cost, single-use, multifunction patient valve for use in such equipment.

2. Discussion of the Prior Art

A variety of medical diagnostic equipment is available in the marketplace for measuring and assessing cardiopulmonary performance. The Anderson et al. U.S. Pat. No. 4,463,764 assigned to Medical Graphic's Corporation applicant's assignee, describes a computer-based system capable of measuring certain parameters on a breath-by-breath basis and for computing and presenting most of the important parameters for assessing cardiopulmonary performance.

A more recent system available from Medical Graphics Corporation is described in the Snow et al. U.S. Pat. No. 4,796,639. This system includes lung measurement equipment for providing data to a computer during testing of the patient. For example, a volume measuring device such as a body plethysmograph provides an input relating to slow vital capacity, residual volume, thoracic gas volume, total lung capacity, and alveolar volume. Equipment is also available for measuring respiratory gas flow, allowing a determination of forced vital capacity, forced expiratory volume and related flow parameters to be measured. In addition, that system permits diffusion measurements so that the ability of the lungs to transfer gas can be assessed. Respiratory pressure is also a meaningful parameter in diagnostic work.

Equipment of the type described requires a patient to inhale and exhale in a controlled fashion as normal air or other gases are introduced. For example, when conducting the diffusion testing, the patient is first asked to exhale as completely as possible and then a suitable gas mixture, such as CO and Neon in air, is inspired from a gas source. Following inspiration, the patient is made to hold his breath for a precise time period during which the CO gas is being absorbed by the blood through the lung tissue. Following that prescribed time interval, the patient exhales into a sample tube. Knowing the amount of CO initially inhaled and the amount finally exhaled to the sample tube allows a computation to be made of the amount of gas transferred through the lungs to the blood. A measurement of the dilution of Neon which does not diffuse through the lung tissue can be used to determine alveolar volume.

A related procedure called nitrogen washout is used to actually assess a patient's lung volume. Here, a patient is made to breathe air normally and then the air supply is blocked and pure oxygen is made available through a demand valve. The patient continues to breathe pure oxygen for period of time sufficient to eliminate all nitrogen from the expired breath. By measuring the total amount of nitrogen gas expired during this interval, lung volume can be assessed in that it is known what the proportion of nitrogen is in normal air in the lungs at a given pressure and temperature.

The device used to control the routing of inspired and expired air and/or other gases in the desired manner for accomplishing the diffusion test and the nitrogen washout test involves the use of a so-called patient valve. When it is recognized that the given patient must both inhale and exhale through the patient valve, there is a need for ensuring that cross-contamination between successive patients using the equipment is eliminated. Because, in the past, such patient valves tend to be quite complex and therefore costly, it has been impractical to treat them as a disposable item. Moreover, prior art valve systems have required cumbersome cleaning operations involving disassembly and reassembly and have been difficult to clean and/or completely sterilize between uses.

Jaeger Medical Instruments of Rockford, Illinois offers a system which it refers to as the "MasterLab" multi-purpose diffusion testing system. It incorporates a specially designed patient valve block that it advertises as being fully sterilizable. Because of complexities, it cannot economically be treated as a "disposable." It comprises a plastic block having a series of interconnected bores formed therein along with appropriate shutters and seals to effect gas routing in a desired fashion. To adequately sterilize the device requires the submersion of the valve assembly in a sterilent for a predetermined time, followed by drying and reinstallation into the test equipment. This necessarily limits the availability of the equipment in running tests on a series of patients and is wasteful of professional time.

Another manufacturer of patient valves is Hans Rudolph, Inc. Its Model 4200 pneumatic mouthshutter and its line of directional control valves, for example, involves relatively costly precision parts including pneumatic actuated pistons, seals and balloon valve assemblies. It cannot be autoclaved and must be disassembled to allow exposure to gas or cold liquid sterilents.

It is accordingly a principle object of the present invention to provide an improved patient valve for use in the cardiopulmonary test equipment.

Another object of the invention is to provide a patient valve which can be manufactured at sufficiently low cost that it can be discarded after a single use.

Still another object of the invention is to provide a replaceable patient valve which can readily be installed in cardiopulmonary performance analyzing equipment by semi-skilled personnel rapidly and reliably so as not to impair the quality of the measurements being taken.

Yet another object of the present invention is to provide a patient valve that obviates the need for any filters to prevent patient cross-examination, thus maintaining unrestricted gas flow through the valve body when the valve structure is "open".

SUMMARY OF THE INVENTION

In accordance with the present invention, the patient valve for use in cardiopulmonary test apparatus comprises a molded, flexible, elastomeric tubular body having a cruciform shape defining intersecting stem and cross-piece portions. Affixed to one end of the stem is a patient mouth piece, forming part of a flow meter, and the other end of the stem portion is open to the ambient. One end of the cross-piece portion is coupled to a demand valve through which a gas other than air is introduced into the patient during inspiration. The other end of the cross-piece member is coupled to a patient circuit including a sample tube having a one-way valve through which expired gases pass in going to a sampling chamber. This molded, tubular, elastomeric body is positioned adjacent first and second selectively actuable clamping means, which are arranged to cooperate with segments of the stem portion having a reduced thickness. Activation of the clamping means causes the stem portion to be pinched closed, thereby blocking the flow of fluid at the location being pinched.

The clamping means preferably comprises a linear actuator, such as a piston, having a movable rod which cooperates with a back-up member such that when the piston is actuated either pneumatically, hydraulically or electrically, the tube becomes closed off to flow until the clamp is released.

A further feature of the clamping means is the fact that the plunger and the back-up member are slidingly affixed to a base such that self-centering of the clamping member takes place relative to the compressible stem portion of the patient valve.

DESCRIPTION OF THE DRAWINGS

Further features, objects and advantages of the invention will become apparent to those skilled in the art from the following detailed description of a preferred embodiment, especially when considered in conjunction with accompanying drawings in which like numerals in the several views refer to corresponding parts.

DESCRIPTION OF THE PREFERRED EMBODIMENT

Figure 1:
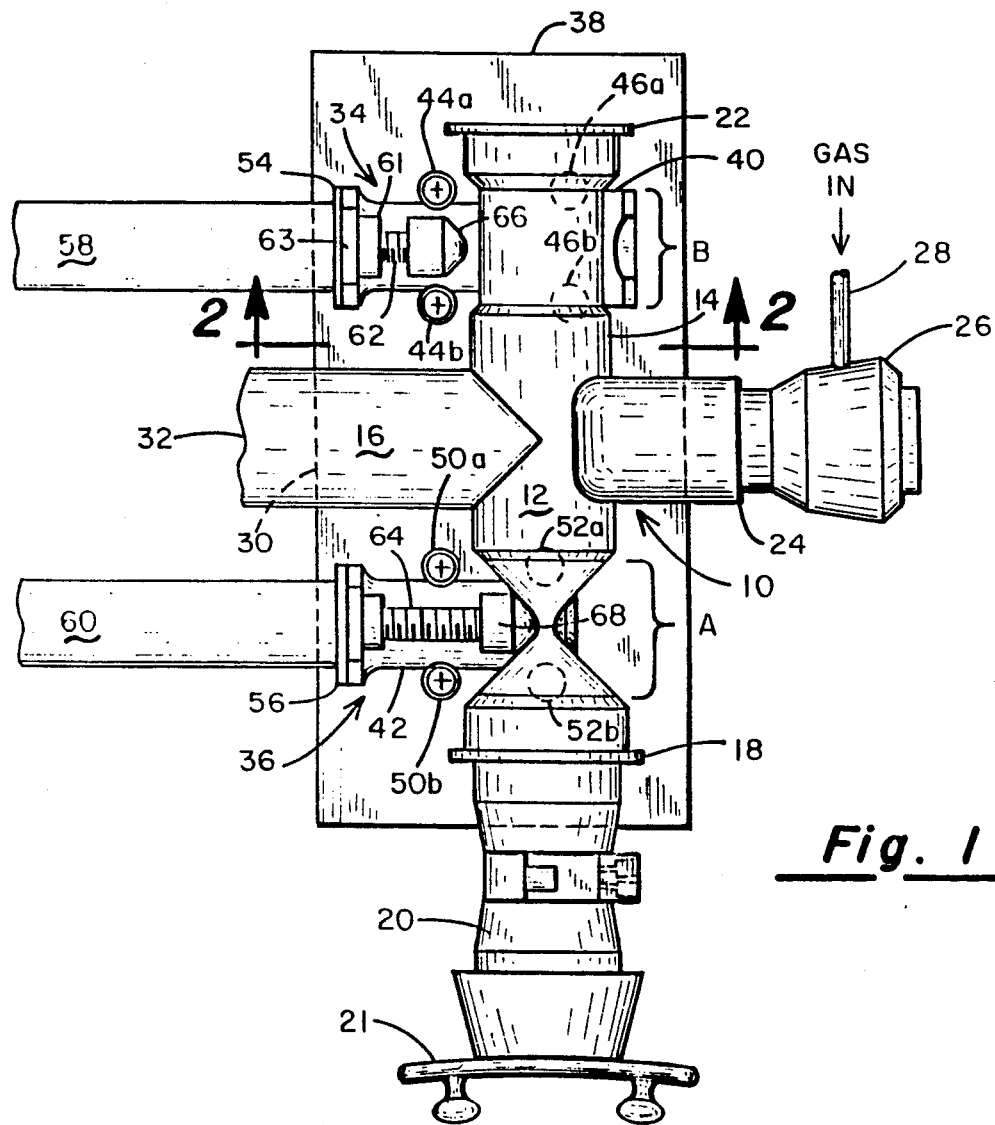
FIG. 1 is a plan view of the patient valve in accordance with present invention.

Referring first to FIG. 1, there is indicated generally by numeral 10 a patient valve constructed in accordance with the present invention for use in cardiopulmonary test apparatus. It is seen to comprise a tubular body 12 formed from a thermoplastic elastomer in a molding process and is generally cruciform in its configuration, including a stem portion 14 and a cross-piece portion 16 intersecting at generally right angles. With no limitation intended, the thermoplastic elastomer may be that sold by the Shell Oil Corporation under the designation "KRATON-D." The wall thickness of the cross-piece 16 is uniform but the wall thickness of the stem portion 14 is of reduced thickness in the zones identified by the brackets labeled A and B. For example, the wall thickness of the tubular cross piece 16 may be 93 mils as is the wall thickness of the stem portion 14 except in zones A and B where the thickness is reduced to 31 mils. It is found that the KRATON-D material with the thickness indicated is generally self-supporting and will not collapse of its own weight.

The stem portion 14 has a first end 18 into which is fitted a flow meter 20. The flow meter 20 may be the device described in U.S. Pat. No. 5,038,773 of John A. Norlien et al., entitled Flow Meter System. As is described in that patent, the flow meter 20, when coupled to appropriate electronic circuitry, can be used to measure the flow rate of respiratory gases either inspired or expired. An appropriate mouth piece or similar patient interface 21 can be attached to the flow meter 20. The other end 22 of the stem portion 14 of the tubular body 12 is opened to the ambient air.

The cross-piece 16 of the valve body 12 has first end 24 into which is fitted a demand valve 26 which regulates the flow of gas introduced into the tube 28. The demand valve 26 is of the type used with scuba gear and, as such, allows gas to flow therethrough only in one direction and only when a negative pressure is created by the lungs when a patient with the mouth piece 21 in his mouth inhales. The other end 30 of the cross-piece portion 16 connects via tubing 32 to a sampling chamber.

Figure 2:
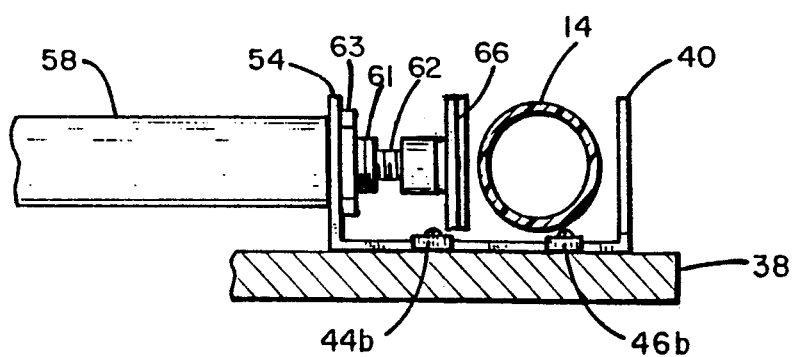
FIG. 2 is a cross sectional view taken along the line 2—2 in FIG. 1.

As shown in FIGS. 1 and 2, the patient valve body 12 cooperates with selectively actuatable clamping means, indicated generally by numerals 34 and 36. Specifically, a base plate 38 is provided and slidingly mounted thereon are first and second U-shaped brackets 40 and 42, respectively. The brackets 40 and 42 are able to slide relative to the base plate 38 by virtue of being mounted between opposed pairs of low friction slotted supports 44a–44b, 46a–46b, 50a–50b and 52a–52b. These supports allow the U-shaped brackets 40 and 42 to freely slide back and forth relative to the base plate 38.

Mounted to the left hand upwardly extending legs 54 and 56 of the U-shaped brackets 40 and 42 are linear actuators 58 and 60 having reciprocably movable plunger rods 62 and 64, respectively. They are preferably mounted by having a threaded collar as at 61 extending through a hole (not shown) in the leg 54 and a nut 63 screwed into the collar. These linear actuators may either comprise electric solenoids or, alternatively, may be hydraulic or pneumatic cylinders, which, in any event, when energized will result in the rods 62 and 64 being extended outward from their respective coil or cylinder, as the case may be. The rods 62 and 64 are threaded to receive a clamping head member as at 66 and 68.

With reference to FIG. 1, linear actuator 58 is shown in its de-energized position whereas linear actuator 60 is shown in its actuated position. When an appropriate electrical, hydraulic or pneumatic input is applied to the linear actuator 60, the head 68 on the rod 64 moves to the right until it contacts the exterior wall of the valve body 12 in the zone labeled "A" which is of reduced wall thickness. Because of the manner in which the linear actuator 60 is mounted on the U-shaped bracket 42, as the plunger head 68 moves further to the right and engages the wall of the valve body, an equal and opposite force acts on the U-shaped bracket 42 and it moves to the left such that the wall of the tube is pinched closed generally along the center line of the stem portion 14. This self-centering action reduces any undue stretching of the elastomeric material which would be the case if the plunger head 68 was required to traverse the entire width dimension of the stem portion 14 to press the walls together against a stationary stop member.

To better understand how the patient valve of the present invention is used in cardiopulmonary test equipment, first consider its use in carrying out a lung diffusion test. As already indicated, the first step is to insert a flow meter 20 into the end 18 of the stem portion 14 of the cruciform tubular valve body 12. Likewise, a demand valve 26 is inserted into the end 24 of the cross-piece 16 and a gas collection tube 32 is inserted into the other end 30 of the cross-piece. The elastomeric valve may now be laid in position in the U-shaped brackets 40 and 42 of the clamping means 34 and 36. The equipment is now ready to execute the diffusion test sequence.

Initially, the patient is asked to breathe normally through the flow meter 20. At this time, both clamping members 34 and 36 are deactivated and, thus, the patient breathes air from the ambient through the end 22 of the patient valve. Next, the clamping means 34 is activated to cause the plunger head 66 to move to the right as the U-shaped bracket 40 moves to the left. A point is reached where the walls of the elastomeric valve body in zone B are pinched together. Now, rather than breathing air when inhaling, the patient will be made to draw a carbon monoxide containing mixture from a gas supply (not shown) through the tube 28 and the demand valve 26 into the lungs. At this point, the clamping means 36 is activated whereby the plunger of the linear actuator 60 moves to the right and cooperates with the end of the U-shaped bracket 42 to close off the valve body in zone "A". The patient is thus forced to hold his or her breath.

This condition is maintained for a predetermined period of time during which the inhaled carbon monoxide diffuses through the lung tissue into the blood. Following the termination of a predetermined delay period, only the clamping means 36 is released, opening up the path through the valve body in zone A and allowing the patient to exhale through the collection tube 32. Clamping means 34 is then reopened, again allowing the patient to breathe ambient air.

By computing the amount of carbon monoxide in the collected sample and knowing the gas volume drawn through the flow meter 20 into the patient's lungs, the difference represents the amount of gas diffused through the lung tissue and the ability of the lungs to function as a gas transfer media can be determined.

When using the patient valve arrangement of the present invention to perform a nitrogen washout test to assess lung volume, again, initially, the clamping means 34 and 36 associated with the valve body are deactivated, allowing the patient to breathe normally ambient air from the end of the tube body 22 through the mouth piece 21 and flow meter 20. This will ensure that the lungs are receiving ambient air with the expected nitrogen content therein. Next, clamping means 34 is actuated to close off the valve body in zone B. As the patient continues to breathe, pure oxygen is made to enter the patient's lungs through line 28 and the demand valve 26. The exhaled breath flows through the cross-piece portion of the valve body to the collection tube 32. The patient is made to breathe pure oxygen for a sufficiently long time to completely eliminate all nitrogen from the lungs. At that point, clamping means 34 is released allowing the patient to breathe ambient air through the stem portion 14 of the elastomeric valve body.

By keeping track of the amount of nitrogen collected during the nitrogen washout test, functional residual capacity (FRC) at the time that clamping means 34 closes can be inferred because the amount of nitrogen in ambient air is a relative constant at a given pressure and temperature.

Those skilled in the art can appreciate that following a given test, it is a relatively simple matter to remove the elastomeric valve body 12 and discard it. A new, clean valve body can be reinserted simply and easily. The mouth piece/flow meter member would be replaced with a new clean one and because all wetted areas have been replaced, there is no possibility for cross-contamination of patients by airborne or moisture borne pathogens. Also, because no protective filters are required, the air ways in the equipment remain open and exhibit very low flow resistance. This, of course, is an advantage in that the test equipment does not adversely impact the patient's respiratory performance.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. Thus, in the illustrated embodiment, the valve body 12 is described as being molded from a suitable thermoplastic elastomeric material with walls of reduced thickness proximate the location of the linear actuators. Those skilled in the art will recognize that it is also possible to have a valve body with uniform wall thickness but alter the elastic properties of the body at the clamping site so as to be more easily stretched to a closed disposition. Furthermore, portions of the valve body can be rigid or inflexible so long as the clamping zones involve a material that can be deformed to close off fluid flow by the clamping structures.

What is claimed is:

1. A disposable patient valve for use in cardiopulmonary test apparatus comprising:
   (a) a unitary, hollow, elastomeric body, said body including at least four tubular sections, one end of each tubular section joined and sealed in a common area to the other three tubular sections to allow fluid flow from any tubular section to any other tubular section without escaping from said body, at least two of said tubular sections including zones in which said body is sufficiently elastic to close when squeezed and reopen when released; and
   (b) first and second selectively actuable clamping means operatively positioned relative to said zones on said two sections to permit said elastomeric body to be inserted and removed from said clamping means when said clamping means is unactuated, the actuation of said clamping means pinching said zones to occlude fluid flow across the location being pinched.

2. The patient valve as in claim 1 wherein the zones of said two sections of said elastomeric body are of increased elasticity proximate the location of said first and second clamping means relative to the remainder of said elastomeric body.

3. The patient valve is in claim 1 wherein the zones of said two sections of said elastomeric body are of greater flexibility relative to the remainder of said elastomeric body.

4. The patient valve as in claim 1 and further including means for coupling a mouth piece member to one of said two tubular sections, the other of said two tubular sections being open to the ambient.

5. The patient valve as in claim 1 and further including means for coupling a gas demand valve to one of said four tubular sections other than said two tubular sections and a gas collection means to the other of said four tubular sections other than said two tubular sections.

6. The patient valve as in claim 1 wherein the zones of said two tubular sections are of reduced thickness proximate the location of said first and second clamping means relative to the remainder of said elastomeric body.

7. The patient valve as in claim 1 wherein said clamping means comprises: a base plate; a back-up member slidingly joined to said base plate; and a linear actuator coupled to said back-up member where the linear actuator and the back-up member are respectively positioned on opposite sides of said two tubular sections proximate said zones.

8. The patient valve as in claim 7 wherein said linear actuator is a fluid actuated piston contained within a cylinder.

9. The patient valve as in claim 7 wherein said linear actuator is an electric solenoid.

10. The patient valve as in claim 7 wherein said back-up member is attached to said linear actuator and slidable relative to said base plate so as to be self-centering relative to said two tubular sections when said linear actuator is operative to clamp said zones of said two tubular sections.

11. The patient valve as in claim 7 wherein the zones of said two tubular sections disposed between said linear actuator and said back-up member are of increased elasticity relative to that of the remainder of said elastomeric body.

12. The patient valve as in claim 7 wherein the zones of said two tubular sections are of greater flexibility relative to the remainder of said elastomeric body.

13. The patient valve as in claim 7 wherein the zones of said two tubular sections disposed between said linear actuator and said back-up member are of reduced thickness relative to that of the remainder of said elastomeric body.

* * * * *